US00PP23913P2

(12) United States Plant Patent
van der Meer et al.

(10) Patent No.: US PP23,913 P2
(45) Date of Patent: Sep. 17, 2013

(54) ***ALOE* PLANT NAMED 'TIKI TAHI'**

(50) Latin Name: *Aloe variegata*
Varietal Denomination: Tiki Tahi

(76) Inventors: Paulus A. M. van der Meer, Monster (NL); Adrianus L. M. van der Meer, Monster (NL)

( * ) Notice: Subject to any disclaimer, the term of this patent is extended or adjusted under 35 U.S.C. 154(b) by 71 days.

(21) Appl. No.: 13/373,738

(22) Filed: Nov. 28, 2011

(51) Int. Cl.
*A01H 5/00* (2006.01)

(52) U.S. Cl.
USPC ..... Plt./373; Plt./372

(58) Field of Classification Search
USPC ..... Plt./372, 373
See application file for complete search history.

(56) References Cited

PUBLICATIONS

UPOV-PLUTO—plant variety database, 201206, citation for cultivar name 'Tiki Tahi'.*

* cited by examiner

*Primary Examiner* — Susan McCormick Ewoldt
(74) *Attorney, Agent, or Firm* — C. A. Whealy

(57) ABSTRACT

A new and distinct cultivar of *Aloe* plant named 'Tiki Tahi', characterized by its compact and upright plant habit; leaves arranged in a dense basal rosette; green-colored leaves with white-colored spots and margins; upright flowering stems; and good postproduction longevity.

3 Drawing Sheets

Botanical designation: *Aloe variegata.*
Cultivar denomination: 'Tiki Tahi'.

BACKGROUND OF THE INVENTION

The present Invention relates to a new and distinct cultivar of *Aloe* plant, botanically known as *Aloe variegata* and hereinafter referred to by the name 'Tiki Tahi'.

The new *Aloe* plant is a product of a planned breeding program conducted by the Inventors in Monster, The Netherlands. The objective of the breeding program is to develop new stemless *Aloe* plants with attractive leaves.

The new *Aloe* plant originated from a cross-pollination in May, 1996 of an unnamed proprietary selection of *Aloe variegata*, not patented, as the female, or seed, parent with a proprietary selection of *Aloe variegata* identified as code number AA21, not patented, as the male, or pollen, parent. The new *Aloe* plant was discovered and selected by the Inventors as a single flowering plant from within the resultant progeny of the cross-pollination in a controlled greenhouse environment in Monster, The Netherlands in October, 1998.

Asexual reproduction of the new *Aloe* plant by cuttings in a controlled greenhouse environment in Monster, The Netherlands since May, 1999 has shown that the unique features of this new *Aloe* plant are stable and reproduced true to type in successive generations.

SUMMARY OF THE INVENTION

Plants of the new *Aloe* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Tiki Tahi'.

These characteristics in combination distinguish 'Tiki Tahi' as a new and distinct *Aloe* plant:

1. Compact and upright plant habit.
2. Leaves arranged in a dense basal rosette.
3. Green-colored leaves with white-colored spots and margins.
4. Upright flowering stems.
5. Good postproduction longevity.

Plants of the new *Aloe* differ primarily from plants of the female parent selection primarily in the following characteristics:

1. Plants of the new *Aloe* are more compact than plants of the female parent selection.
2. Rosette of leaves of plants of the new *Aloe* is denser than rosette of leaves of plants of the female parent selection.
3. Leaf spots of plants of the new *Aloe* are circular in shape whereas leaf spots of plants of the female parent selection are oval in shape.

Plants of the new *Aloe* differ primarily from plants of the male parent selection primarily in the following characteristics:

1. Leaves of plants of the new *Aloe* are shinier than leaves of plants of the male parent selection.
2. Leaf margins of plants of the new *Aloe* are almost entire whereas leaf margins of plants of the male parent selection are serrate.
3. Leaves of plants of the new *Aloe* have more distinct spots than leaves of plants of the male parent selection.

Plants of the new *Aloe* can be compared to plants of *Aloe* 'Cosmo', not patented. Plants of the new *Aloe* differ from plants of 'Cosmo' in the following characteristics:

1. Leaves of plants of the new *Aloe* are longer and narrower than leaves of plants of 'Cosmo'.
2. Leaves of plants of the new *Aloe* have more distinct spots than leaves of plants of 'Cosmo'.

DESCRIPTION OF THE PHOTOGRAPHS

The accompanying colored photographs illustrate the overall appearance of the new *Aloe* plant showing the colors as true as it is reasonably possible to obtain in colored reproductions of this type. Colors in the photographs may differ slightly from the color values cited in the detailed botanical description which accurately describe the colors of the new *Aloe* plant.

The photograph on the first sheet comprises a side perspective view of a typical flowering plant of 'Tiki Tahi' grown in a container.

The photograph on the second sheet comprises a top perspective view of the leaves of a typical plant of 'Tiki Tahi'.

The photograph on the third sheet is a close-up view of a typical inflorescence of 'Tiki Tahi'.

DETAILED BOTANICAL DESCRIPTION

The aforementioned photographs and following observations and measurements describe plants that were grown during the autumn in 9-cm containers in a glass-covered greenhouse in Monster, The Netherlands and under cultural conditions typically used in *Aloe* production. During the production of the plants, day temperatures ranged from 17° C. to 21° C. and night temperatures ranged from 15° C. to 19° C. Plants were seven months old when the photographs and description were taken. In the following description, color references are made to The Royal Horticultural Society Colour Chart, 2007 Edition, except where general terms of ordinary dictionary significance are used.

Botanical classification: *Aloe variegata* 'Tiki Tahi'.

Parentage:

*Female, or seed, parent*.—Unnamed proprietary selection of *Aloe variegata*, not patented.

*Male, or pollen, parent*.—Proprietary selection of *Aloe variegata* identified as code number AA21, not patented.

Propagation:

*Type*.—By cuttings.

*Time to initiate roots, summer*.—About 20 days at temperatures of 19° C. to 24° C.

*Time to initiate roots, winter*.—About 30 days at temperatures of 17° C. to 19° C.

*Root description*.—Medium in thickness, fleshy; yellowish brown in color.

*Rooting habit*.—Moderately freely branching; dense.

Plant description:

*Plant form and growth habit*.—Upright flowering plant; leaves arranged in a dense basal rosette; plants stemless; single erect flowering stem.

*Plant height, soil level to top of flowers*.—About 22 cm.

*Plant height, soil level to top of foliar plane*.—About 9.2 cm.

*Plant diameter*.—About 12 cm.

*Leaves*.—Arrangement and quantity: Simple, arranged in a basal rosette, sessile; about 33 leaves per plant. Length: About 7.7 cm. Width: About 2.7 cm. Thickness: About 8 mm. Shape: Narrowly deltoid, subulate. Apex: Narrowly apiculate. Base: Broadly cuneate. Margin: Entire to finely denticulate. Texture, upper and lower surfaces: Glabrous, verrucose; succulent. Color: Developing leaves, upper surface: Close to N137C to N137D; towards the base, close to 146D; margins and spots, close to NN155C. Developing leaves, lower surface: Close to 147A; towards the base, close to 152B to 152C; margins and spots, close to NN155D. Fully expanded leaves, upper surface: Close to N137C to N137D and 147A; towards the base, close to 197C to 197D; margins and spots, close to NN155C. Fully expanded leaves, lower surface: Close to N137C to N137D and 147A; towards the base, close to N170D; margins and spots, close to NN155D.

Flower description:

*Flower shape and arrangement*.—Tubular flowers arranged in terminal raceme; about 28 flowers develop per inflorescence.

*Fragrance*.—None detected.

*Natural flowering season*.—Plants flower from midsummer to late autumn in The Netherlands.

*Postproduction longevity*.—Flowers last about one week on the plant; flowers not persistent.

*Flower buds*.—Length: About 2.1 cm. Diameter: About 4 mm. Shape: Narrowly oblong, slightly curved downwards. Color, upper surface: Close to 42B to 42C; stripes, close to 198A to 198B. Color, lower surface: Close to 22D; sutures, close to 144D.

*Inflorescence height*.—About 9.9 cm.

*Inflorescence width*.—About 7.2 cm.

*Flower size*.—Diameter: About 6 mm. Length (height): About 3.5 cm.

*Perianth*.—Quantity and arrangement: Six tepals per flower; tepals mostly fused, segments free at upper 10% of the tepal. Tepal length: About 3.5 cm. Tepal width: About 3 mm. Tepal shape: Narrowly oblong. Tepal apex: Broadly acute. Tepal margin: Entire. Tepal texture, upper and lower surfaces: Smooth, glabrous; velvety. Tepal color, upper tepals: When opening, upper surface: Close to 39B; towards the apex, tinged with close to 147C. When opening, lower surface: Close to 35C; stripes, close to 41B. Fully opened, upper surface: Close to 39B; towards the apex, tinged with close to 147C; stripes, close to 42D; color becoming closer to 37A with development. Fully opened, lower surface: Close to 35C; stripes, close to 41B. Tepal color, lower tepals: When opening, upper surface: Close to 24D; stripes, close to 144B. When opening, lower surface: Close to 27B; stripes, close to 146D. Fully opened, upper surface: Close to 27A to 27B; stripes, close to 144B; color becoming closer to 150D with development. Fully opened, lower surface: Close to 27B; stripes, close to 146D.

*Peduncles*.—Angle: Mostly erect. Strength: Moderately strong. Length: About 24.5 cm. Diameter: About 5 mm. Texture: Smooth, glabrous. Color: Close to 152A to 152B.

*Pedicels*.—Angle: About 60° from vertical. Strength: Moderately strong. Length: About 7 mm. Diameter: About 1.5 mm. Texture: Smooth, glabrous. Color: Upper surface, close to 34B; lower surface, close to 152D.

*Reproductive organs*.—Stamens: Quantity per flower: About six. Filament length: About 2.9 cm. Filament color: Close to 37C to 37D. Anther length: About 2 mm. Anther shape: Narrowly oblong. Anther color: Close to N25A to N25B. Pollen amount: Moderate to abundant. Pollen color: Close to 5B. Pistils: Quantity per flower: One. Pistil length: About 2.6 cm. Style length: About 2.6 mm. Style color: Close to 36C. Stigma shape: Pointed. Stigma color: Close to 36D. Ovary color: Close to 143C.

*Seeds and fruits*.—Seed and fruit development have not been observed on plants of the new *Aloe*.

Disease & pest resistance: Resistance to pathogens and pests common to Oriental Lilies has not been observed.

Temperature tolerance: Plants of the new *Aloe* have been observed to tolerate high temperatures of about 45° C. and to be hardy to USDA Hardiness Zone 10.

It is claimed:

1. A new and distinct *Aloe* plant named 'Tiki Tahi' as illustrated and described.

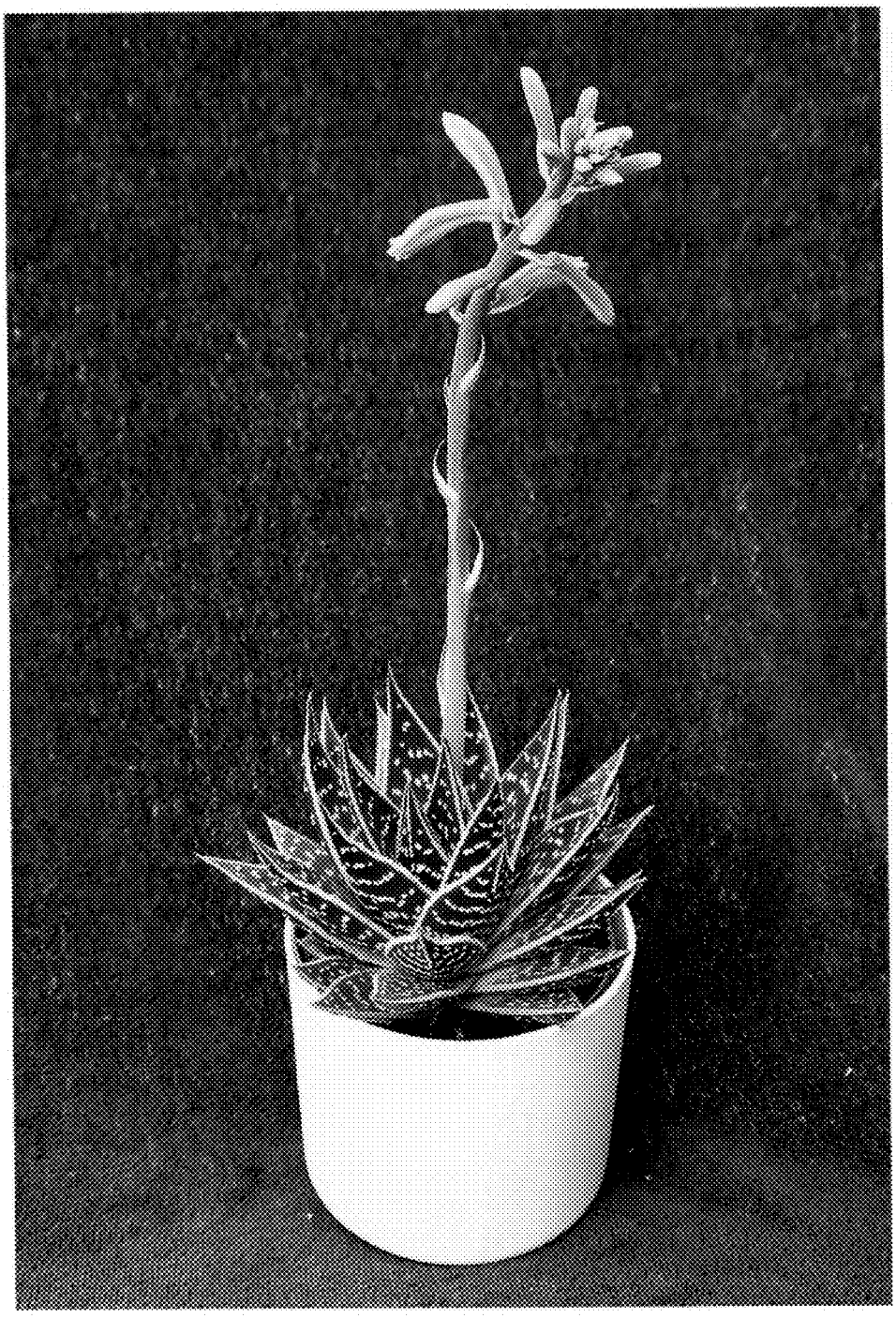

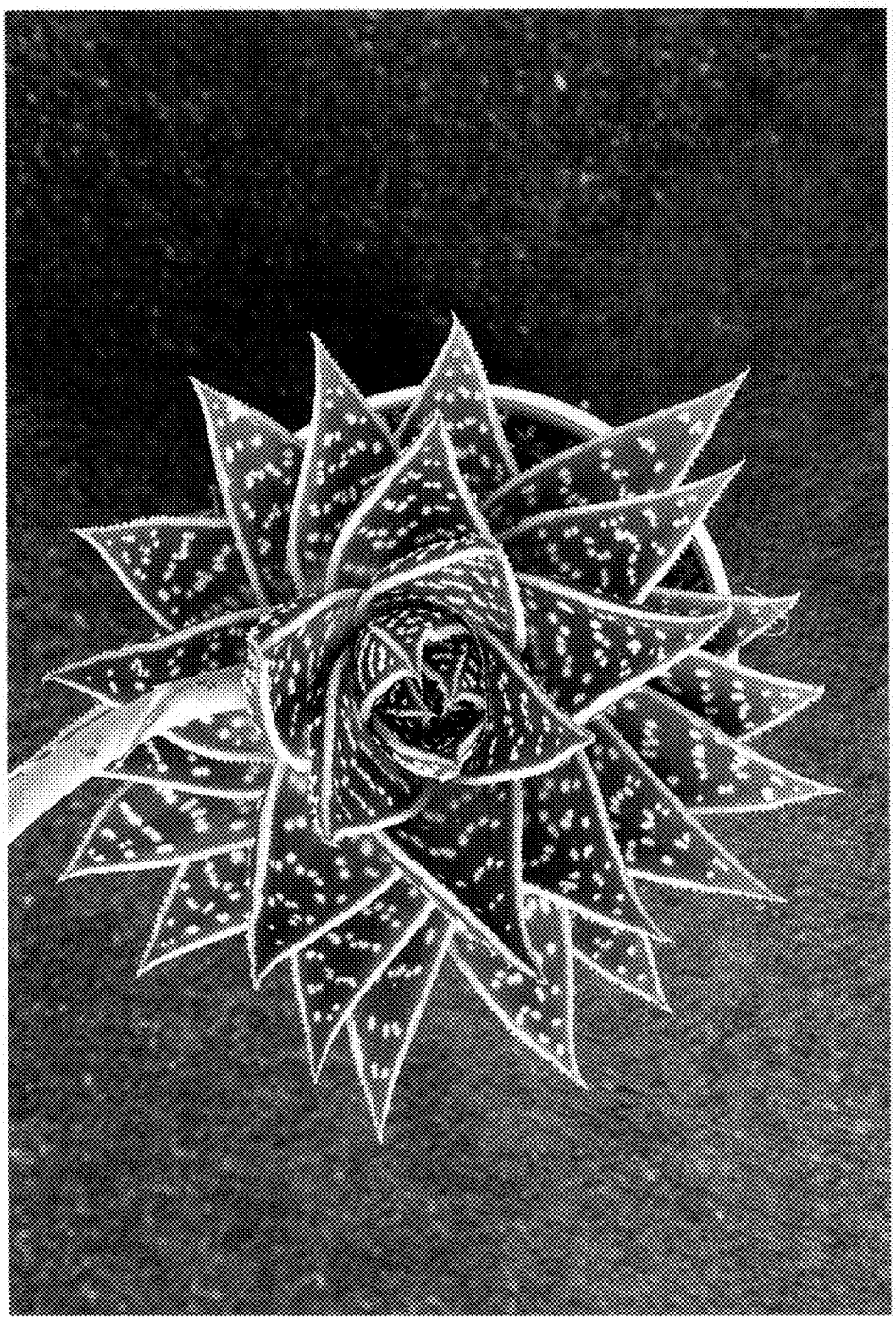

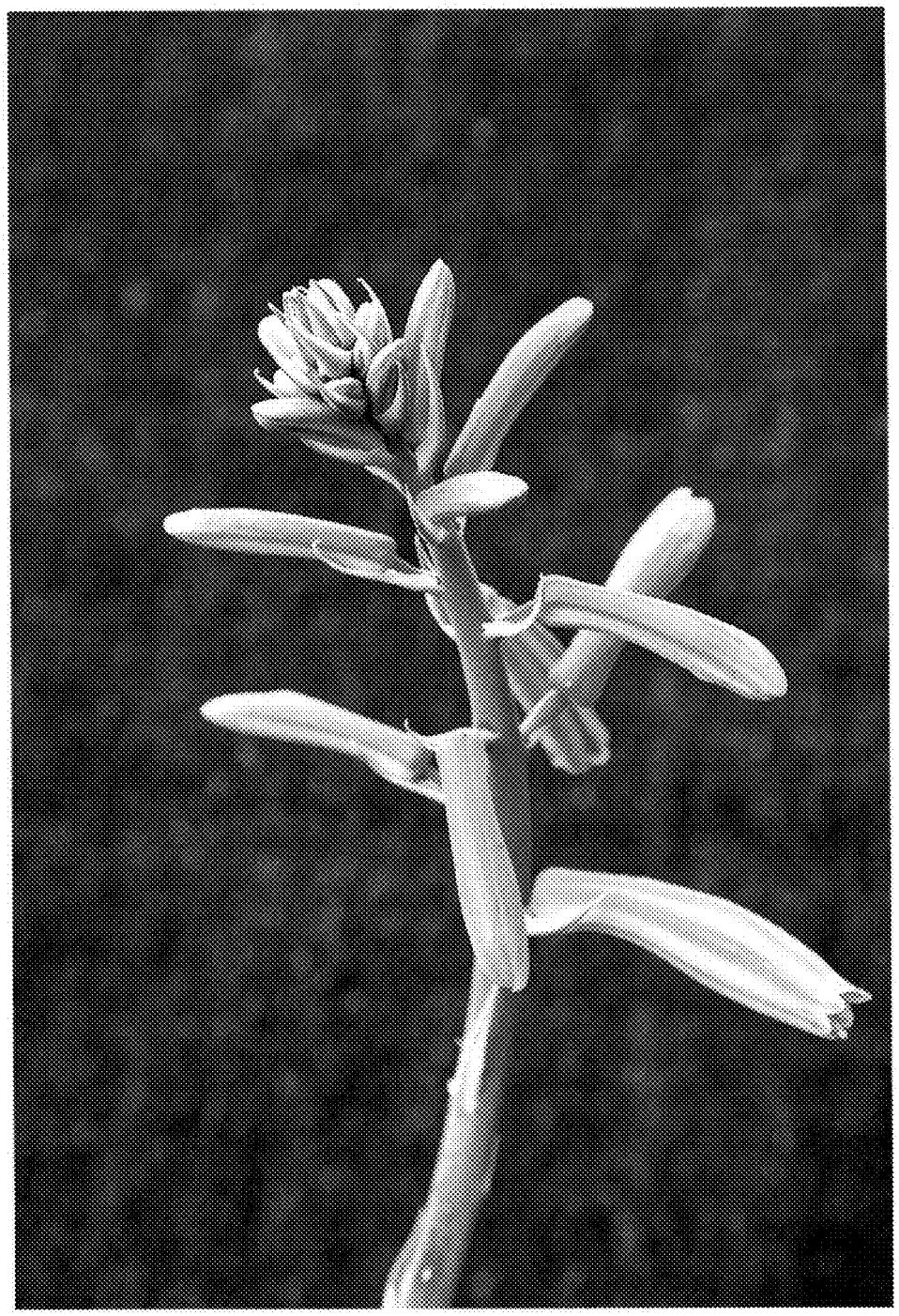

* * * * *